(12) United States Patent
Graf et al.

(10) Patent No.: US 9,855,093 B2
(45) Date of Patent: Jan. 2, 2018

(54) INSTRUMENT FOR CUTTING BODY TISSUE

(71) Applicant: BOWA-ELECTRONIC GMBH & CO. KG, Gomaringen (DE)

(72) Inventors: Thomas Graf, Reutlingen (DE); Alexander Doppelstein, Bodelshausen (DE); Carolin Spuentrup, Saarbruecken (DE); Karl-Guenter Noe, Cologne (DE)

(73) Assignee: BOWA-ELECTRONIC GMBH & CO. KG, Gomaringen (DE)

( * ) Notice: Subject to any disclaimer, the term of this patent is extended or adjusted under 35 U.S.C. 154(b) by 434 days.

(21) Appl. No.: 14/410,250

(22) PCT Filed: Jul. 10, 2013

(86) PCT No.: PCT/EP2013/064593
§ 371 (c)(1),
(2) Date: Dec. 22, 2014

(87) PCT Pub. No.: WO2014/009420
PCT Pub. Date: Jan. 16, 2014

(65) Prior Publication Data
US 2015/0366606 A1    Dec. 24, 2015

(30) Foreign Application Priority Data
Jul. 12, 2012   (DE) ......................... 10 2012 013 738

(51) Int. Cl.
*A61B 18/14*    (2006.01)
*A61B 17/42*    (2006.01)
(Continued)

(52) U.S. Cl.
CPC .......... *A61B 18/1485* (2013.01); *A61B 17/42* (2013.01); *A61B 2017/4225* (2013.01);
(Continued)

(58) Field of Classification Search
CPC .. A61B 2017/4225; A61B 2018/00202; A61B 18/1485; A61B 2018/00559; A61B 17/42
(Continued)

(56) References Cited

U.S. PATENT DOCUMENTS 5,032,124 A * 7/1991 Menton .................. A61B 18/24
                                                   606/14
5,047,042 A * 9/1991 Jerath .................... A61B 17/42
                                                   600/564
(Continued)

OTHER PUBLICATIONS

"Reduktion der Spottingrate nach laparoskopischer suprazervikaler Hysterektomie"—Banerjee C., et al.—Geburtsh Frauenheilk 2010—pp. 798-802.
(Continued)

*Primary Examiner* — Linda Dvorak
*Assistant Examiner* — Ryan T Clark
(74) *Attorney, Agent, or Firm* — Gerald E. Hespos; Michael J. Porco; Matthew T. Hespos

(57) ABSTRACT

An instrument for cutting body tissue has an instrument shaft, A blade, is adjacent to a distal end of the instrument shaft and can be folded out with respect to a longitudinal axis of the shaft and can be rotated about the longitudinal axis. An operating part is at a proximal end of the instrument shaft. A proximal end of the blade directed toward the operating part can be pivoted laterally out away from the longitudinal axis about an end of the blade that faces away from the proximal end and that is distally articulated at an articulation point. A tissue stop is arranged at the distal end of the instrument shaft. The tissue stop can be brought into an active position in which a stop surface facing the blade in the proximal direction has a specified fixed distance from the articulation point.

12 Claims, 5 Drawing Sheets

(51) Int. Cl.
*A61B 18/00* (2006.01)
*A61B 90/00* (2016.01)

(52) U.S. Cl.
CPC ............ *A61B 2018/00559* (2013.01); *A61B 2018/00601* (2013.01); *A61B 2018/1412* (2013.01); *A61B 2018/1475* (2013.01); *A61B 2090/0801* (2016.02)

(58) Field of Classification Search
USPC .......................................................... 606/47
See application file for complete search history.

(56) References Cited

U.S. PATENT DOCUMENTS

| | | | | |
|---|---|---|---|---|
| 5,554,159 | A * | 9/1996 | Fischer | A61B 18/14 606/45 |
| 5,676,663 | A * | 10/1997 | Kim | A61B 18/1485 606/45 |
| 5,951,550 | A * | 9/1999 | Shirley | A61B 18/1485 600/564 |
| 6,309,388 | B1 * | 10/2001 | Fowler | A61B 18/1485 600/564 |
| 6,641,581 | B2 | 11/2003 | Muzzammel | |
| 6,730,085 | B2 * | 5/2004 | George | A61B 18/1485 600/564 |
| 2002/0072761 | A1 * | 6/2002 | Abrams | A61B 17/062 606/190 |
| 2003/0109873 | A1 * | 6/2003 | Muzzammel | A61B 18/14 606/45 |
| 2004/0002701 | A1 | 1/2004 | Ryan et al. | |
| 2006/0094983 | A1 | 5/2006 | Burbank et al. | |
| 2012/0143209 | A1 * | 6/2012 | Brecheen | A61B 17/42 606/119 |

OTHER PUBLICATIONS

International Search Report dated Nov. 22, 2013.
English Translation of International Preliminary report on patentability for PCT/EP2013/064593.

* cited by examiner

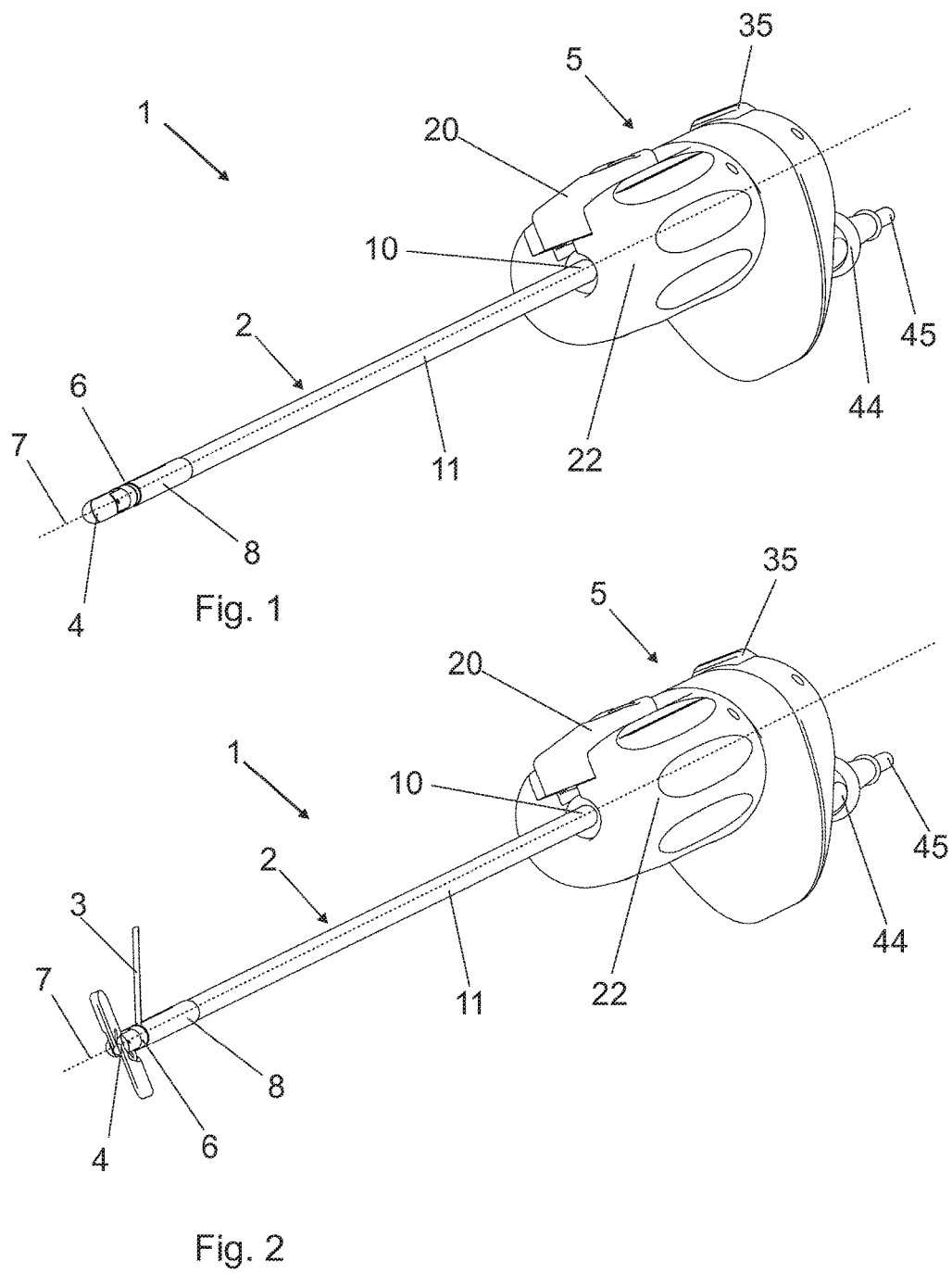

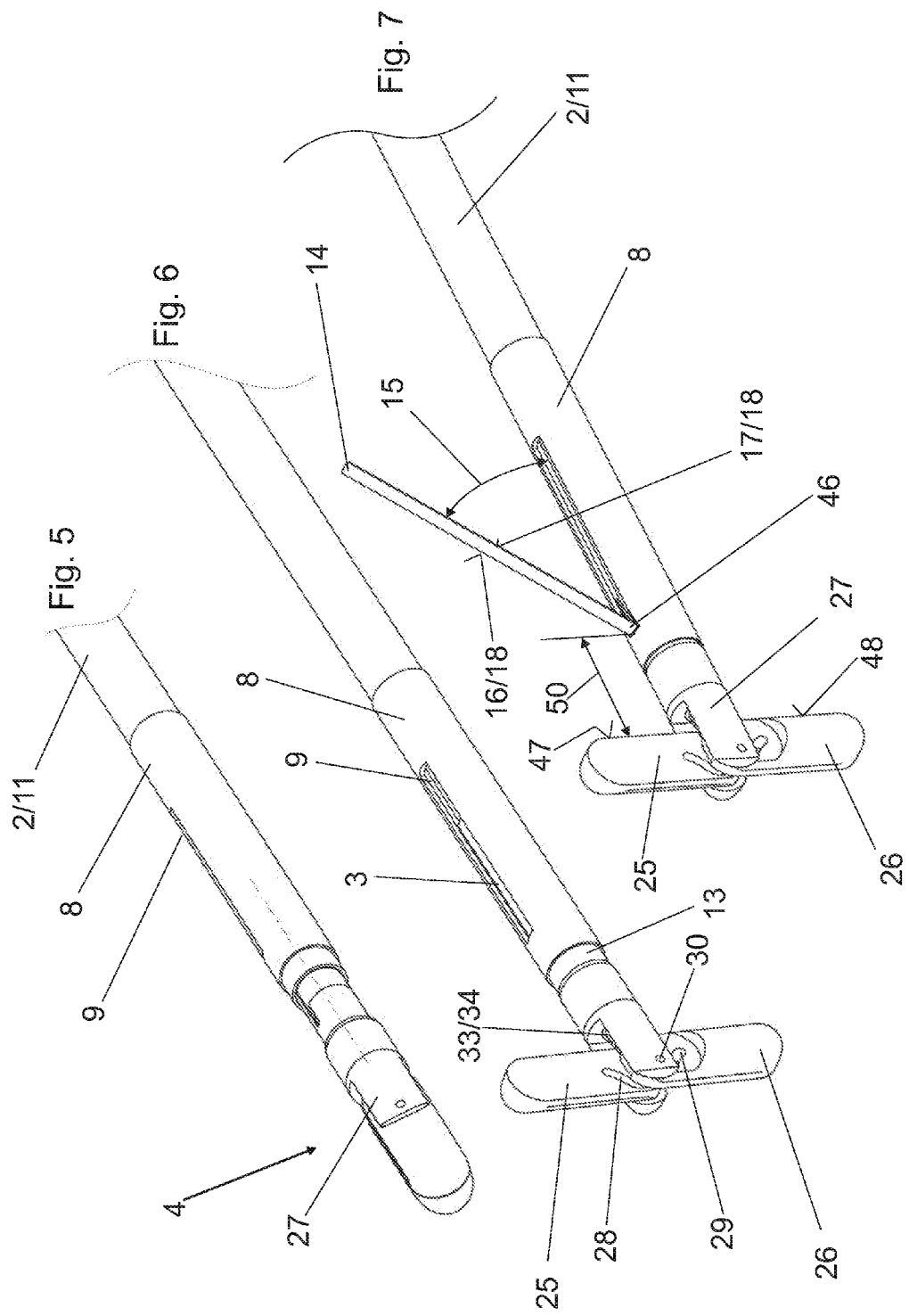

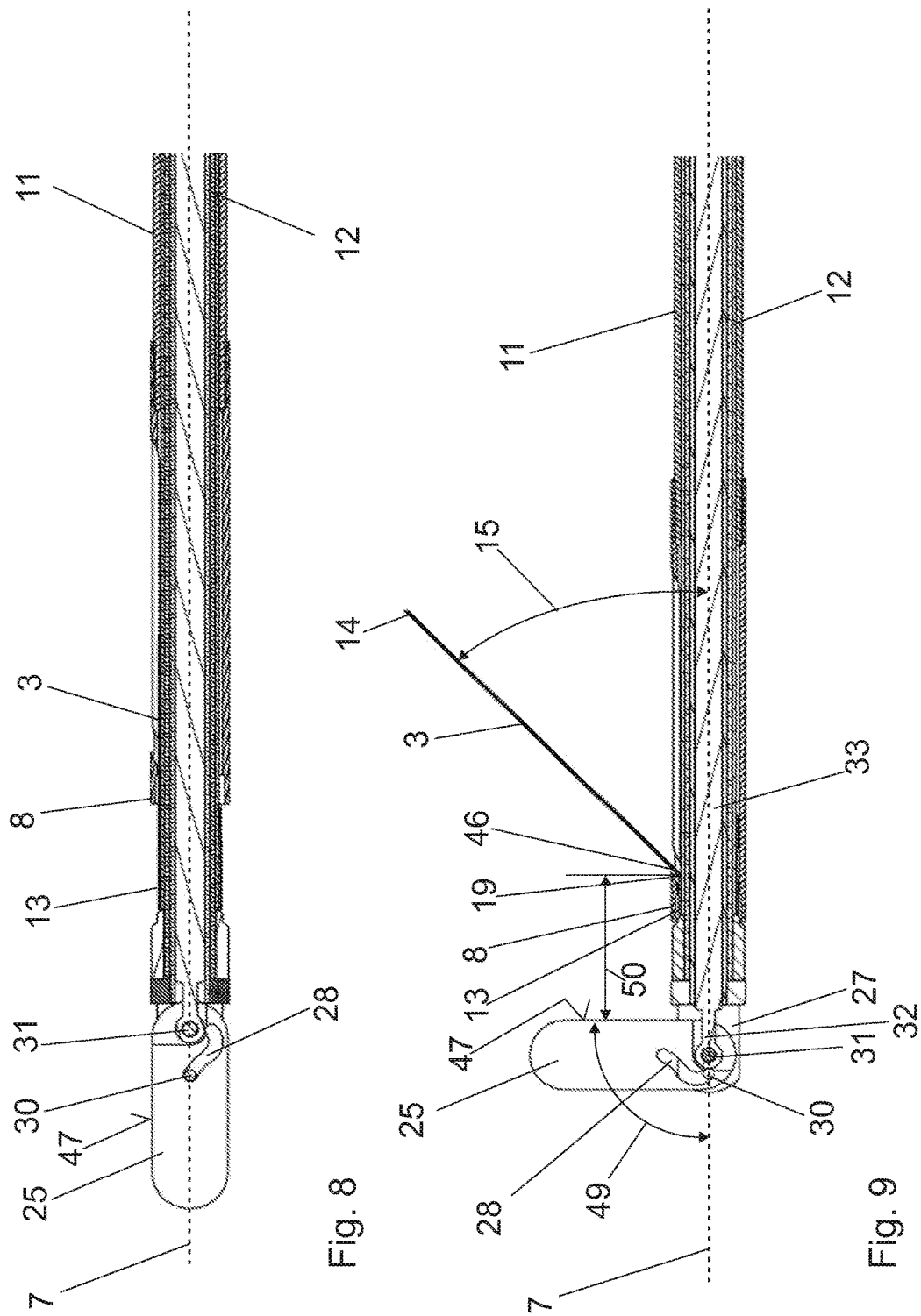

INSTRUMENT FOR CUTTING BODY TISSUE

BACKGROUND

Field of the Invention

The invention relates to an instrument for cutting body tissue, comprising
an instrument shaft,
a blade, which is arranged adjacent to the distal end of the instrument shaft and can be folded out with respect to a longitudinal axis of the shaft and can be rotated about the longitudinal axis, and
an operating part arranged at the proximal end of the instrument shaft.

Description of the Related Art

From Banerjee C., Kaiser N., Hatzmann W., Reiss G., Schmitz J., Hellmich M., Noé G. "Reduktion der Spottingrate nach laparoskopischer suprazervikaler Hysterektomie" (Lower Spotting Rates after Laparoscopic Supracervical Hysterectomy) Geburtsh Frauenheilk 2010; 70: 798-802 it is a known procedure to perform deep-cone excision of the cervical canal endoscopically and additionally to coagulate the remaining portion of the cervical canal by applying an electric current. The conical endoscopic excavation of the cervical stump allows better detection of endometrioid cells in the isthmic and cervical region than coagulation alone. In this procedure, suprapubic access to the cervical canal by means of a trocar or trocar sleeve offers certain advantages compared to vaginal access to the cervical canal, such as a low spotting rate.

From US 2012/0143209 A1, a medical instrument for a laparoscopic supracervical hysterectomy (LASH) is known. The known instrument for cutting body tissue comprises an instrument shaft, a blade, which is arranged adjacent to the distal end of the instrument shaft and which can be folded out or pivoted out with respect to a longitudinal axis of the shaft and can be rotated about the longitudinal axis, and an operating part arranged at the proximal end of the instrument shaft.

The disadvantage here is that this instrument is not suitable for suprapubic access to the cervical canal via a known laparoscopic trocar or trocar sleeve.

Furthermore, from US 2006/09490083 A1 a tissue stop arranged at a distal shaft end is known, which is designed as a four lever parallelogram that can be pivoted out laterally around an axis arranged transverse to the longitudinal axis, in such a way that two each of the levers can be folded out laterally transverse to the longitudinal axis.

From U.S. Pat. No. 6,641,581 B2 an instrument for cutting body tissue is known that comprises an instrument shaft with a longitudinally displaceable and rotatable electrode array protruding at the distal end thereof and with a curved arm protruding laterally at the distal end thereof, said arm extending a cutting electrode.

The disadvantage here is that, due to the rigid laterally protruding arm, the distal end of the instrument shaft or the electrode array respectively, is not well-suited for insertion through a trocar sleeve into a body cavity with tissue to be cut. Another disadvantage is that this instrument does not comprise a tissue stop.

From US 2004/002701 A1 a shaft end with two jaws is known that can be folded out laterally. These jaws are designed as an ultrasound device emitting in distal direction. Therefore, a person skilled in the art would not consider the replacement of the mechanical tissue stop from D1 with the jaws known from D4 as common practice.

The object of the present invention is to provide an instrument that is particularly suited for the cone-shaped excavation of the cervix and that allows suprapubic access to the cervix by means of a laparoscopic or trocar sleeve.

SUMMARY OF THE INVENTION

An instrument for cutting body tissue has an instrument shaft. A blade is arranged at a distal end of the instrument shaft and can be folded out with respect to a longitudinal axis of the shaft and can be rotated about the longitudinal axis. An operating part is at a proximal end of the instrument shaft. The distal end of the instrument shaft can be inserted into a body cavity with tissue to be cut, through a trocar sleeve. A proximal end of the blade directed toward the operating part can be laterally pivoted out away from the longitudinal axis about an end of the blade that faces away from the proximal end and that is distally articulated to an articulation point An outer sleeve rotatable about the longitudinal axis is arranged at the distal end of the instrument shaft, said outer sleeve having a lateral opening transverse to its longitudinal direction from which the blade can be pivoted out.

By means of the laterally pivotable or foldable (pivotable and foldable are used synonymously in the following) blade which, for example, can be designed as a knife or as a (high frequency) cutting electrode, and the tissue stop which can be brought into an active position with a predetermined fixed distance to the articulation point, the instrument shaft, i.e., the distal end thereof, can, in a non-active starting position, e.g., with the tissue stop not unfolded, be inserted easily into a body cavity with tissue to be cut, e.g. a cervical canal, via a suitable conventional trocar sleeve. In the process, the tissue stop can be folded out for example laterally into its active position and the instrument can be locked in its position.

By means of the tissue stop, the intended cutting position of the blade can thus be fixed or ensured.

The blade can be folded out or pivoted out from the lateral opening of the rotatable outer sleeve into an intended position and can be turned by rotating the blade around the longitudinal axis of the instrument shaft so that the surrounding tissue is cut out in a conical shape.

According to a preferred embodiment of the invention, the fixed distance between the stop surface of the tissue stop in its active position (e.g. at the wall of the Portio vaginalis) and the articulation point of the blade is greater than 1.5 mm. As a result, for example, in the case of so-called LASH conization, this will guarantee the reliable removal of the mucosa in the cervical canal. A fixed distance of about 4 to 20 mm, and preferably 12 mm, has proved to be especially appropriate. To adapt to anatomical conditions, greater or smaller distances are also possible.

According to a further preferred embodiment of the invention, the tissue stop folds out into its active position about a first transverse axis which is arranged at the distal end of the instrument shaft. The tissue stop can thus be folded out from the longitudinal axis into its active position from a starting position arranged in the longitudinal direction. In the active position, the rear, i.e. proximally directed stop surface can have an angle of preferably 90 degrees relative to the longitudinal axis. However, intermediate positions and angles greater than 90 degrees are possible as well.

According to a preferred embodiment of the invention, the blade has a cutting edge on at least one of its two longitudinal sides that extend parallel to the longitudinal axis.

With the sharp cutting edge, the blade forms a knife that is rotatable around the longitudinal axis and with which a tissue cone can be mechanically excised. By means of a coagulation electrode or laser radiation, the cut tissue surface can be coagulated.

According to a further preferred embodiment of the invention, the instrument shaft comprises an outer shaft tube whose distal end is connected to the outer sleeve, and wherein an inner shaft tube is arranged in the outer shaft tube. Between the outer sleeve and the inner shaft tube an inner sleeve is arranged having the blade on its proximal end face. The inner sleeve is thus rotatable around the inner shaft tube together with the outer sleeve and the outer shaft tube. Furthermore, the outer shaft tube with the outer sleeve is longitudinally displaceable with respect to the inner shaft tube and the inner sleeve.

Insofar as the blade is spring-mounted at its distally articulated end, the lateral opening of the outer sleeve can be brought into alignment with the proximal end of the blade by displacing the outer shaft tube with the outer sleeve, so that, due to the spring effect, the blade's proximal end folds out or pivots out of the lateral opening. By retracting the outer shaft tube with the outer sleeve, the articulated end of the blade is covered and the blade is folded into the opening again. The proximal end of the blade is preferably designed as a free end, but can in principle also be connected to a longitudinally displaceable joint arrangement or the like.

According to a further preferred embodiment of the invention, the inner sleeve and the blade are formed from a shape memory alloy at least in the region of their articulation point. The shape memory alloy is designed in such a way that a predetermined fully extended position is the preferred position, with the free end of the blade being "folded in" by covering it with the outer sleeve, and with the free end, upon release, folding out into its predetermined extended position.

According to a further preferred embodiment of the invention, a longitudinally displaceable first operating element is arranged on the operating part, and the outer shaft tube with the outer sleeve is displaceable in order to actuate the blade, i.e., to fold the blade out or in. The operating element is lockable in different locking positions. By locking the first operating element, the blade can be fixed between a retracted and fully extended position at different angles relative to the longitudinal axis.

According to a further embodiment of the invention, a second rotatable operating element is arranged on the operating part and with it the outer shaft tube with the blade folded out from the outer sleeve can be rotated around the longitudinal axis of the instrument shaft. By rotating the blade around the longitudinal axis, a tapered or cone-shaped tissue portion can thus be easily excised.

According to a further preferred embodiment of the invention, the blade is designed as an electrode. By connecting the blade to an active terminal of a high-frequency generator, while connecting the patient to a large-surface neutral electrode, an electrosurgical cut can be performed. Furthermore, with the flat side of the blade the contacted tissue can be coagulated.

Instead of a large-surface neutral electrode, the tissue stop may also be designed as an electrode which is connected to the high-frequency generator, with the blade and the tissue stop forming a bipolar electrode pair.

According to a further preferred embodiment of the invention, the tissue stop comprises two jaws with mirror-symmetrically designed guide grooves arranged in a U-shaped, i.e. forked, mounting bracket at the distal end of the instrument shaft. The jaws with their guide grooves are pivotable opposite to each other around a first transverse axis arranged in the mounting bracket transversely to the longitudinal axis, with the jaws being connected at their proximal ends, via a second transverse axis arranged parallel to the first transverse axis, to a distal end of a longitudinally displaceable lifting rod positioned in the inner shaft tube. By longitudinally displacing the lifting rod in the distal direction, the second transverse axis is thus moved in the direction of the fixed first transverse axis so that the jaws, similar to the jaws of forceps, open outward in the radial direction and close by moving the lifting rod in the proximal direction.

According to a further preferred embodiment of the invention, in the operating part the proximal end of the lifting rod facing away from its distal end is operatively connected to a third operating element. The tissue stop can thus be locked in different locking positions via the third operating element.

The instrument according to the invention for cutting body tissue is particularly suited as a laparoscopic instrument for cutting and/or coagulating the inner portio.

With both the blade and tissue stop retracted, i.e. in a starting position, the instrument can be inserted into the cervical canal through a trocar sleeve and further through the portio. The tissue stop can be folded out and pulled against the portio. After unfolding the blade and activating the electric current, the cutting is performed by rotating the outer shaft tube together with the outer sleeve and the inner sleeve, while the tissue stop with the inner shaft tube does not co-rotate. After folding/pivoting the blade and the tissue stop back in, the instrument can be extracted from the trocar sleeve. For example, the blade can be pivoted at an angle between 0 and 45°. Thus, a precise adjustment of the tissue ablation can be ensured. The precise positioning is supported by the rear stop of the tissue stop at the portio entrance.

BRIEF DESCRIPTION OF THE DRAWINGS

FIG. 1 a three-dimensional representation of an instrument for cutting body tissue with the blade pivoted in and the tissue stop folded in, i.e., blade and tissue stop are in a starting position.

FIG. 2 a three-dimensional representation of the instrument of FIG. 1 with the blade pivoted out and the tissue stop folded out.

FIG. 5 a three-dimensional representation of the distal end of FIG. 1 with the tissue stop folded in (starting position) and the blade pivoted in.

FIG. 6 a three-dimensional representation of the distal end of FIG. 5 with the tissue stop folded out (active position) and the blade pivoted in.

FIG. 7 a three-dimensional representation of the distal end of FIG. 5 with the tissue stop folded out (active position) and the blade pivoted out.

FIG. 8 a cross-sectional lateral view of the distal end of FIG. 5.

FIG. 9 a cross-sectional lateral view of the distal end of FIG. 7.

DETAILED DESCRIPTION OF THE PREFERRED EMBODIMENTS

Figure 3:
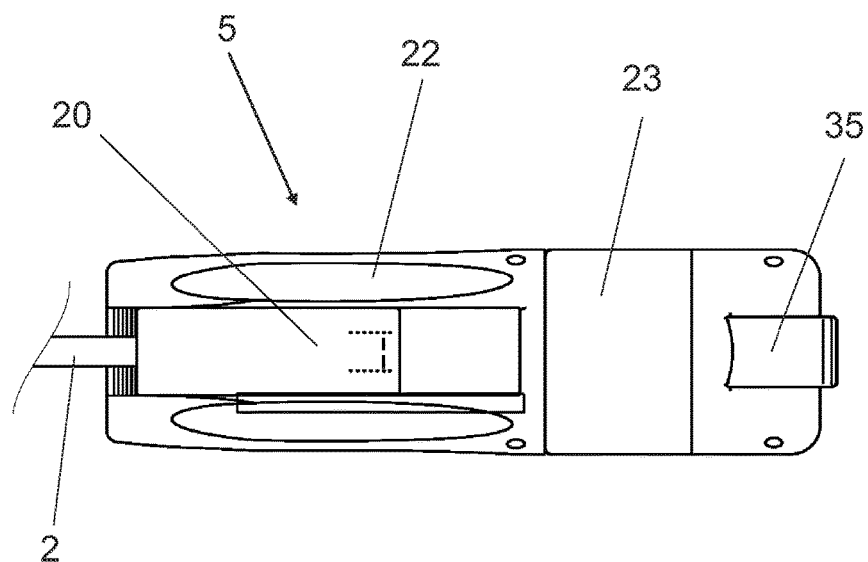
FIG. 3 a top view of the operating part of FIG. 1.
Figure 4:
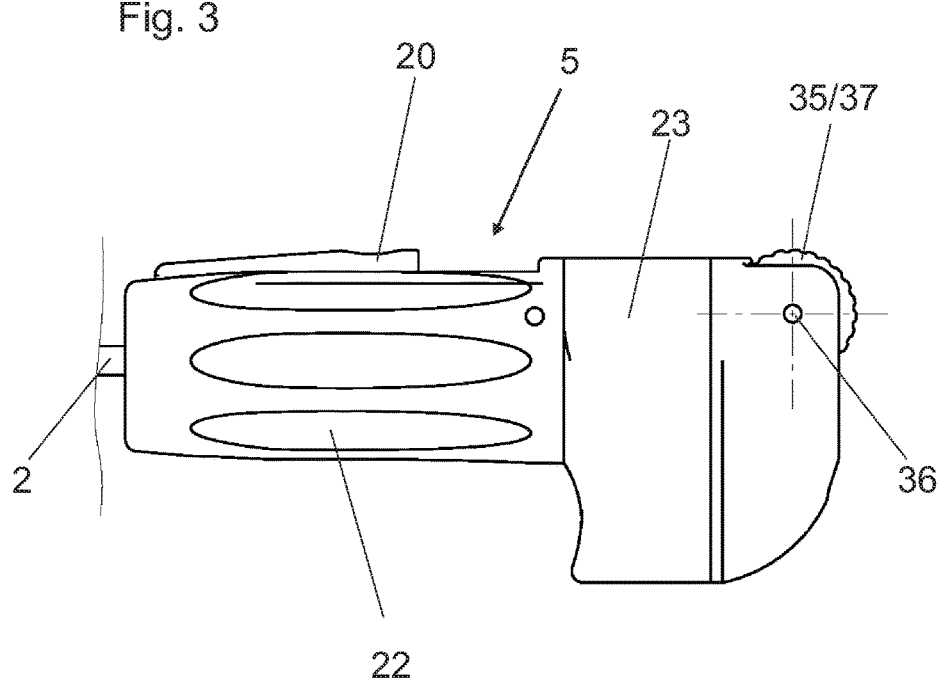
FIG. 4 a side view of the operating part of FIG. 3.
Figure 10:
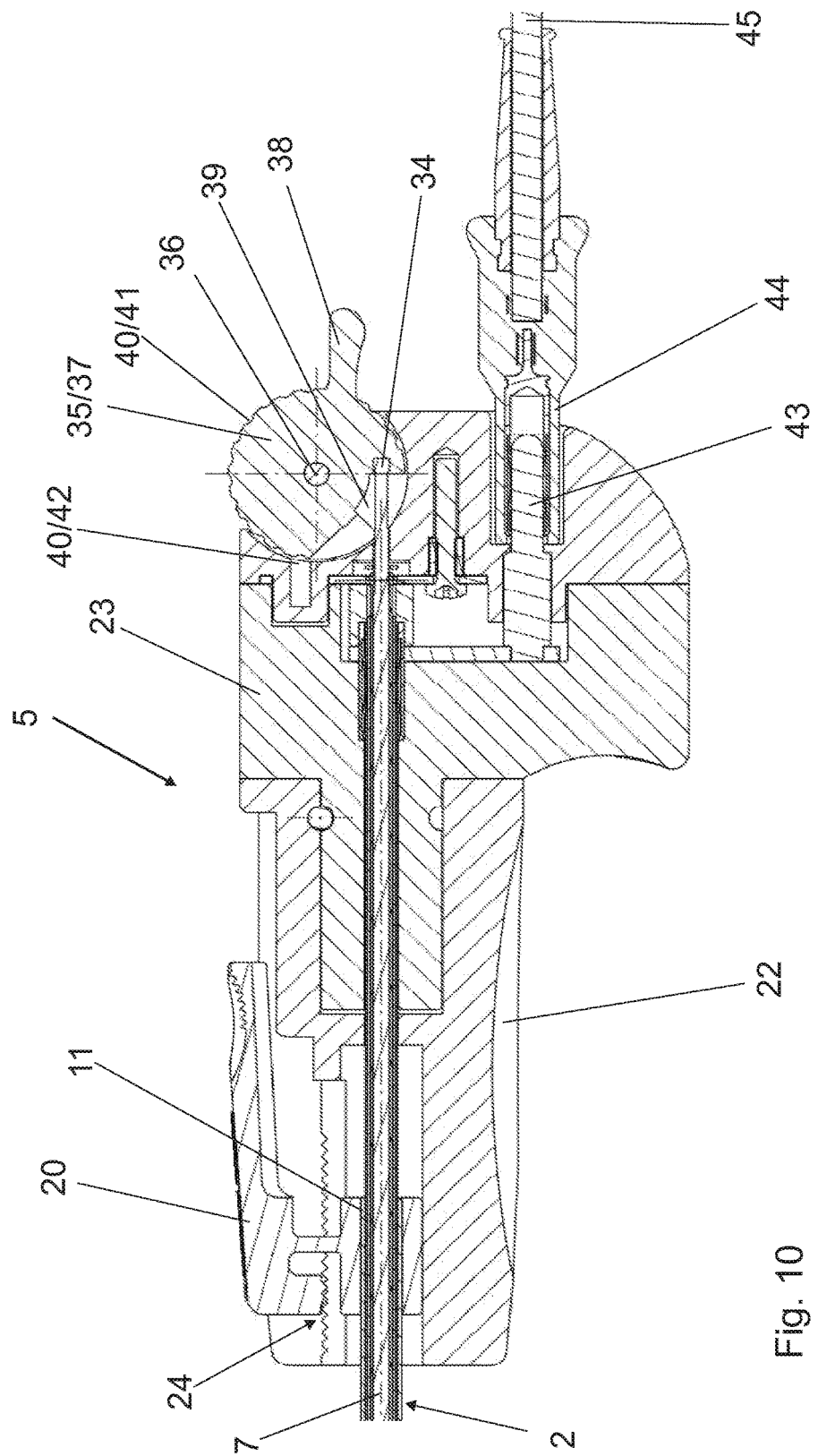
FIG. 10 an enlarged and cross-sectional lateral view of the operating part of FIG. 1.

Identical reference symbols in the figures indicate identical or analogous elements. The following description refers to all Figures, unless exclusive reference is given to a specific Figure.

An instrument 1 for cutting body tissue comprises primarily an instrument shaft 2, a blade 3, a tissue stop 4 and an operating part 5.

At a distal end 6 of the instrument shaft 2 facing away from the surgeon, an outer sleeve 8 is arranged which can be rotated around a longitudinal axis 7 of the instrument shaft 2, said outer sleeve 8 having a lateral opening, i.e. a rectangular aperture, namely a kind of window, transverse to its longitudinal axis. Facing the surgeon, at its proximal end 10 the instrument shaft 2 possesses the operating part 5. The instrument shaft 2 consists of an outer shaft tube 11 and an inner shaft tube 12 which is movable (longitudinally displaceable and rotatable) within the outer shaft tube 11.

For cleaning purposes, the distal end 6 of the outer shaft tube 11 is detachably connected to the proximal end 10 of the outer sleeve 8 by a connecting thread. Between the outer sleeve 8 and the inner shaft tube 12, an inner sleeve 13 is arranged, which, at its proximal end face, merges into the blade 3. When the lateral opening 9 is aligned with the blade 3, the blade 3, which is articulated at its distal end to the inner sleeve 13, folds out through the lateral opening 9 with its proximally free end 14 and forms a maximum pivot angle 15 of, for example, 45° relative to the longitudinal axis 7.

The blade 3 possesses a cutting edge 18 on both of its longitudinal sides 16, 17 extending parallel to the longitudinal axis 7. The inner sleeve 13 and the blade 3 connected thereto are made of a shape memory alloy with the maximum pivot angle 15 being imprinted at the articulation point 19. Shape memory alloys (SMA), which are also referred to as memory metals are known to those skilled in the art. These materials exhibit the phenomenon that they are seemingly able to "remember" their original shape even after considerable deformation. Suitable materials include:

NiTi (nickel-titanium; nitinol)
CuZn (copper-zinc)
CuZnAl (copper-zinc-aluminum)
CuAlNi (copper-aluminum-nickel)
FeNiAl (iron-nickel-alumnium).

The inner sleeve 13 together with the outer sleeve 8 and the outer shaft tube 11 is rotatable around the inner shaft tube 12. The outer shaft tube 11 with the outer sleeve 8 is longitudinally displaceable with respect to the inner shaft tube 12 and the inner sleeve 13. The longitudinal displacement between the outer sleeve 8 and the inner sleeve 13 causes the folding in and folding out of the blade 3 from the lateral opening 9 of the outer sleeve 8.

Via a longitudinally displaceable first operating element 20 arranged on the operating part 5, said operating element 20 being connected to the proximal end 21 of the outer shaft tube 11, the outer sleeve 8 can be moved in the longitudinal direction relative to the inner sleeve 13 with the blade 3 so that the blade 3 is covered at its articulation point 19 and thus folded in/pivoted in, or it is released and thus folded out/pivoted out.

The operating part 5 comprises a second operating element 22 which is mounted rotatably about the longitudinal axis 7 on a main component 23 of the operating part 5, which is firmly attached to the inner shaft tube 12. In the second operating element 22 of the operating part 5, the first operating element 20 is longitudinally displaceable and lockable in different locking positions by means of a locking device 24. By rotating the second operating element 22, the outer shaft tube 11 with the outer sleeve 8 and the first operating element 20 can be rotated around the inner shaft tube 12. By retracting the first operating element 20 in the proximal direction, the blade 3 folds in. By moving the first operating element 20 in the distal direction, the blade folds out/pivots out, depending on how much the lateral opening with the blade is covered. Different locking positions of the first operating element 20 thus result in different pivot angles 15 of the blade 3.

As an extension of the instrument shaft 2, the tissue stop 4 is arranged at the distal end 6 thereof. The tissue stop 4 consists of two jaws 25, 26 that are pivotable opposite to each other and arranged in a U-shaped mounting bracket 27. The jaws 25, 26 each have a guide groove 28, 29. The two guide grooves 28, 29 are designed mirror-symmetrically to one another. The jaws 25, 26 with their guide grooves 28, 29 are thus pivotable opposite to each other around a first transverse axis 30 arranged transversely to the longitudinal axis 7 in the mounting bracket 27. The jaws 25, 26 are connected at their proximal ends via a second transverse axis 31 with the distal end 32 of a lifting rod 33 which is longitudinally displaceable in the inner shaft tube 12. At its proximal end 34, the lifting rod is operatively connected to a third operating element 35 in the operating part 5.

The third operating element 35 is designed as a wheel 37 with a radially arranged operating lever 38, said wheel 37 being rotatable around a third transverse axis 36 which is arranged parallel to the first transverse axis 30 and the second transverse axis 31. The wheel 37 is connected to the proximal end 34 of the lifting rod 33 via a laterally and transversely extending groove 39. With a partial rotation of the wheel 37, the tissue stop 4 can be adjusted via the lifting rod 33 between a starting position with retracted jaws 25, 26 and a fully extended position of the jaws 25, 26. The end and intermediate positions can be fixed by means of a second locking device 40 which is arranged between the third operating element 35 and the operating part 5. For this purpose, the wheel 37 comprises latching grooves 41 on its circumference, into which a spring-mounted latching element 42 can engage. The tissue stop 4 can thus be locked in different locking positions or extended positions.

With their outer edges facing in the folding-out direction the jaws 25, 26 form the stop surfaces 47, 48 which, in their active position, have a fold-out angle 49 of, for example, 90° relative to the longitudinal axis 7 and a fixed distance 50 of >1.5 mm relative to the articulation point 19. In the exemplary embodiments the fixed distance 50 is about 12 mm.

In the exemplary embodiments, the blade 3 is designed as an electrode which is conductively connected to the operating part 5 via a plug contact 43. The plug contact 43 can be connected to a female connector 44 of an electrode cable 45 leading to an electrosurgical unit (not illustrated), namely a high-frequency generator.

Of course, the embodiments discussed in the specific description and shown in the Figures are merely illustrative exemplary embodiments of the present invention. In the light of the present disclosure a person skilled in the art has a broad spectrum of optional variations available.

In particular, the tissue stop 4, which is electrically insulated from the blade 3, can be used as a second electrode so that the tissue stop 4 and the blade 3 form a bipolar electrode pair which can be connected to the high-frequency generator or electrosurgical unit (not illustrated).

LIST OF REFERENCE NUMBERS

1 Instrument
2 Instrument shaft
3 Blade
4 Tissue stop
5 Operating part
6 Distal end of 2
7 Longitudinal axis of 2
8 Outer sleeve
9 Lateral opening of 8
10 Proximal end of 2
11 Outer shaft tube of 2
12 Inner shaft tube of 2
13 Inner sleeve
14 Free end of 3
15 Pivot angle of 3
16 First longitudinal side of 3
17 Second longitudinal side of 3
18 Cutting edge
19 Articulation point of 3
20 First operating element
21 Proximal end of 11
22 Second operating element
23 Main component of 5
24 Locking device of 20, 22
25 First jaw of 4
26 Second jaw of 4
27 U-shaped mounting bracket
28 First guide groove
29 Second guide groove
30 First transverse axis of 27
31 Second transverse axis
32 Distal end of 33
33 Lifting rod
34 Proximal end of 33
35 Third operating element
36 Third transverse axis
37 Wheel of 35
38 Operating lever of 35
39 Groove
40 Second locking device of 35
41 Latch grooves of 40
42 Latching element of 40
43 Plug contact
44 Female connector
45 Electrode cable
46 Distally articulated end of 3
47 First stop surface of 4
48 Second stop surface
49 Fold-out angle of 47, 48
50 Distance

The invention claimed is:

1. An Instrument (1) for cutting body tissue, comprising
an instrument shaft (2) with distal and proximal ends,
a blade (3) arranged adjacent to the distal end (6) of the instrument shaft (2) and configured to be folded out with respect to a longitudinal axis (7) of the shaft (2) and configured to be rotated about the longitudinal axis (7), the blade (3) having a cutting edge (18) on at least one of its two longitudinal sides (16, 17) that extend parallel to the longitudinal axis (7), and
an operating part (5) arranged at the proximal end (10) of the instrument shaft (2),
wherein
the distal end (6) of the instrument shaft (2) is configured to be inserted into a body cavity with tissue to be cut, through a trocar sleeve,
a proximal end (14) of the blade (3) directed toward the operating part (5) is configured to be laterally pivoted out away from the longitudinal axis about an end (46) of the blade that faces away from the proximal end (14) and that is distally articulated at an articulation point (19),
a tissue stop (4) is arranged at the distal end (6) of the instrument shaft (2),
in that the tissue stop is configured to be brought into an active position in which a stop surface (47, 48) facing the blade (3) in the proximal direction has a specified fixed distance (50) from the articulation point (19),
an outer sleeve (8) rotatable about the longitudinal axis (7) is arranged at the distal end (6) of the instrument shaft (2), said outer sleeve having a lateral opening (9) transverse to its longitudinal direction, from which the blade (3) is configured to be pivoted out,
the instrument shaft (2) has an outer shaft tube (11) whose distal end (6) is connected to the outer sleeve (8),
an inner shaft tube (12) is arranged in the outer shaft tube (11),
an inner sleeve (13) having a proximal end face, the inner sleeve (13) is arranged between the outer sleeve (8) and the inner shaft tube (12), the blade (3) being at the proximal end face of the inner sleeve (13),
the inner sleeve (13) together with the outer sleeve (8) and the outer shaft tube (11) are rotatable around the inner shaft tube (12), and
the outer shaft tube (11) with the outer sleeve (8) being longitudinally displaceable with respect to the inner shaft tube (12) and the inner sleeve (13).

2. The instrument of claim 1,
wherein
the fixed distance (50) is greater than 1.5 mm.

3. The instrument of claim 1,
wherein
the tissue stop (4) can be folded out into its active position about a first transverse axis (30) which is arranged at the distal end (6) of the instrument shaft (2).

4. The instrument of claim 1,
wherein
the inner sleeve (13) and the blade (3) are formed from a shape memory alloy at least in the region of their articulation point (19).

5. The instrument of claim 1,
wherein
a longitudinally displaceable first operating element (20) is arranged on the operating part (5) and is movable over the outer shaft tube (11) to operate the blade (3).

6. The instrument of claim 5,
wherein
the first operating element (20) is lockable in different locking positions.

7. The instrument of claim 5,
wherein
a rotatable second operating element (22) is arranged on the operating part (5) the outer shaft tube (11) with the blade (3) pivoted out from the outer sleeve (8) and is rotatable about the longitudinal axis (7).

8. The instrument of claim 1,
wherein
the blade (3) is formed as an electrode.

9. The instrument of claim 1,
wherein the tissue stop (4) at the distal end (6) of the instrument shaft (2) has two jaws (25, 26) arranged in a U-shaped mounting bracket (27) with mirror-symmetrically formed guide grooves (28, 29), the jaws (25, 26) with their guide grooves (28, 29) can be pivoted opposite to each other about a first transverse axis (30) arranged transversely to the longitudinal axis (7) in the mounting bracket (27), and the jaws (25, 26) are connected at their proximal ends via a second transverse axis (31) with a distal end (32) of a longitudinally displaceable lifting rod (33) located inside the inner shaft tube (12).

10. The instrument claim 9,
wherein
the lifting rod (33) at its proximal end (34) facing away from the distal end (32) is operatively connected to a third operating element (35) in the operating part (5).

11. The instrument of claim 10,
wherein
by means of the third operating element (35) the tissue stop (4) is lockable in different locking positions.

12. The instrument of claim 1,
wherein
the tissue stop (4) is formed as an electrode.

\* \* \* \* \*